(12) United States Patent
Copa et al.

(10) Patent No.: US 8,529,590 B2
(45) Date of Patent: Sep. 10, 2013

(54) ANASTOMOSIS DEVICE AND RELATED METHODS

(75) Inventors: Vincent G. Copa, St. Paul, MN (US); Kory P. Hamel, Bloomington, MN (US); Sidney F. Hauschild, Brooklyn Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 1217 days.

(21) Appl. No.: 11/804,114

(22) Filed: May 17, 2007

(65) Prior Publication Data

US 2007/0219584 A1 Sep. 20, 2007

Related U.S. Application Data

(62) Division of application No. 10/646,383, filed on Aug. 21, 2003.

(60) Provisional application No. 60/405,140, filed on Aug. 22, 2002.

(51) Int. Cl.
*A61B 17/08* (2006.01)

(52) U.S. Cl.
USPC ............ 606/153; 606/139; 606/144; 606/151

(58) Field of Classification Search
USPC ...................... 606/144, 151, 153; 600/29–31
See application file for complete search history.

(56) References Cited

U.S. PATENT DOCUMENTS

| | | | |
|---|---|---|---|
| 4,701,162 A | 10/1987 | Rosenberg | |
| 4,705,502 A | 11/1987 | Patel | |
| 4,792,330 A | 12/1988 | Lazarus et al. | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |
| 4,932,956 A | 6/1990 | Reddy et al. | |
| 5,047,039 A | 9/1991 | Avant et al. | |
| 5,123,908 A | 6/1992 | Chen | |
| 5,152,772 A | 10/1992 | Sewell, Jr. | |
| 5,306,226 A * | 4/1994 | Salama | 600/29 |
| 5,540,701 A * | 7/1996 | Sharkey et al. | 606/153 |
| 5,545,171 A | 8/1996 | Sharkey et al. | |

(Continued)

FOREIGN PATENT DOCUMENTS

| | | |
|---|---|---|
| WO | WO 92/04869 | 4/1992 |
| WO | WO 96/07447 | 3/1996 |

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Gary Jackson
*Assistant Examiner* — Diane Yabut
(74) *Attorney, Agent, or Firm* — Kagan Binder, PLLC

(57) ABSTRACT

Described are methods and devices relating to reconnecting the urethra and bladder after a radical prostatectomy, wherein the devices incorporate tissue approximating structure to maintain contact between a severed bladder neck tissue and a severed urethral stump tissue, preferably without the use of sutures.

33 Claims, 17 Drawing Sheets

(56) References Cited

U.S. PATENT DOCUMENTS

| | | |
|---|---|---|
| 5,695,504 A | 12/1997 | Gifford, III et al. |
| 5,707,380 A | 1/1998 | Hinchliffe et al. |
| 5,833,698 A | 11/1998 | Hinchliffe et al. |
| 5,931,842 A | 8/1999 | Goldsteen et al. |
| 5,964,791 A | 10/1999 | Bolmsjo |
| 6,024,748 A | 2/2000 | Manzo et al. |
| 6,119,045 A | 9/2000 | Bolmsjo |
| 6,149,667 A | 11/2000 | Hovland et al. |
| 6,193,734 B1 | 2/2001 | Bolduc et al. |
| 6,238,368 B1 | 5/2001 | Devonec |
| 6,254,570 B1 | 7/2001 | Rutner et al. |
| 6,299,598 B1 | 10/2001 | Bander |
| 6,302,905 B1 | 10/2001 | Goldsteen et al. |
| 6,391,039 B1 | 5/2002 | Nicholas et al. |
| 6,416,545 B1 | 7/2002 | Mikus et al. |
| 6,440,146 B2 | 8/2002 | Nicholas et al. |
| 6,447,533 B1 | 9/2002 | Adams |
| 6,461,367 B1 * | 10/2002 | Kirsch et al. ............ 606/144 |
| 6,485,496 B1 | 11/2002 | Suyker et al. |
| 6,494,908 B1 | 12/2002 | Huxel et al. |
| 6,520,974 B2 | 2/2003 | Tanner et al. |
| 6,530,932 B1 | 3/2003 | Swayze et al. |
| 6,562,024 B2 | 5/2003 | Alvarez de Toledo et al. |
| 6,565,579 B2 | 5/2003 | Kirsch et al. |
| 6,599,311 B1 | 7/2003 | Biggs et al. |
| 6,602,243 B2 | 8/2003 | Noda |
| 6,695,832 B2 | 2/2004 | Schon et al. |
| 6,702,825 B2 | 3/2004 | Frazier et al. |
| 6,719,709 B2 | 4/2004 | Whalen et al. |
| 6,719,749 B1 | 4/2004 | Schweikert et al. |
| 6,726,697 B2 | 4/2004 | Nicholas et al. |
| 6,740,098 B2 | 5/2004 | Abrams et al. |
| 6,746,456 B2 | 6/2004 | Xiao |
| 6,746,472 B2 | 6/2004 | Frazier et al. |
| 6,821,283 B2 | 11/2004 | Barzell et al. |
| 2001/0049492 A1 | 12/2001 | Frazier et al. |
| 2002/0002363 A1 | 1/2002 | Urakawa et al. |
| 2002/0087176 A1 | 7/2002 | Greenhalgh |
| 2003/0069629 A1 | 4/2003 | Jadhav et al. |
| 2003/0208183 A1 | 11/2003 | Whalen et al. |
| 2003/0229364 A1 | 12/2003 | Seiba |
| 2004/0078047 A1 | 4/2004 | Nicholas et al. |
| 2004/0087995 A1 | 5/2004 | Copa et al. |
| 2005/0070938 A1 | 3/2005 | Copa et al. |
| 2005/0131431 A1 | 6/2005 | Copa et al. |
| 2005/0192602 A1 | 9/2005 | Manzo |
| 2005/0251155 A1 | 11/2005 | Orban et al. |

FOREIGN PATENT DOCUMENTS

| | | |
|---|---|---|
| WO | WO 99/16359 | 4/1999 |
| WO | WO 99/21490 | 5/1999 |
| WO | WO 99/21491 | 5/1999 |
| WO | WO 99/58081 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034913 | 4/2004 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

* cited by examiner

ANASTOMOSIS DEVICE AND RELATED METHODS

CROSS-REFERENCE TO RELATED APPLICATIONS

The present application is a divisional of patent application Ser. No. 10/646,383, filed Aug. 21, 2003, which non-provisional Application claims the benefit of commonly assigned provisional Application having Ser. No. 60/405,140, filed on Aug. 22, 2002, and entitled SURGICAL STENT DEVICES AND METHODS, which Applications are incorporated herein by reference in their entireties.

FIELD OF THE INVENTION

The present invention generally relates to methods of reconnecting urethra and bladder tissues after a radical prostatectomy, and related devices. Particular embodiments of the invention relate to methods and devices for performing a vesico-urethral anastomosis.

BACKGROUND

In a radical prostatectomy, the surgeon removes all or most of the patient's prostate. Because the urethra travels through the prostate immediately before reaching the bladder, the upper part of the urethra is removed in the surgery. The procedure leaves a severed urethral stump and a severed bladder neck. To restore proper urinary functions, the bladder and the urethra must be reconnected.

Conventionally, a surgeon may execute delicate suturing operations with tiny, fine needles to reconnect these anatomical bodies. Installation of sutures, however, with a needle, to connect the severed tissues, can be a difficult and often technique-sensitive task. Many factors can make this task difficult, including a very small amount of tissue to work with (at the urethral stump and at the bladder neck), proximal ureters at the bladder, and a proximal nerve bundle and sphincter at the urethral stump. All of these add up to a complicated and delicate suturing procedure that, if not performed properly, could result in complications such as leakage, difficulty in healing or failure to heal, incontinence, or impotence. Specific problems include necrosis of the sutured tissues; stricture of the urethra, which impedes the flow of fluid through it; and a urethra-bladder connection that is not fluid-tight. In addition, methods of suturing the urethra to the bladder allow for accidental or inadvertent piercing of the nearby neurovascular bundle, which can cause incontinence or impotence.

SUMMARY

The invention relates to an anastomosis device that includes a catheter body and tissue approximating structure. The tissue approximating structure can be used to cause or maintain contact between severed portions of tissue to allow or cause the severed tissue surfaces to heal together, instead of using sutures. The device may be used, for example, in performing procedures such as a vesico-urethral anastomosis in association with a radical prostatectomy, or with an end-to-end urethral anastomosis. Advantageously, the device, including the tissue approximating structure, can be left installed during the healing process to function to allow the tissue to heal while at the same time functioning to drain urine from the bladder.

Preferred tissue approximating structure may be remotely actuatable from a retracted position (e.g., within the device) to a position of use, external to the device. As an advantage, embodiments of the tissue approximating structure can be moved and adjusted remotely (e.g., using a an actuating mechanism at the proximal end of the device) during a surgical procedure. The device, overall, thus allows a surgeon to position and re-position a tissue approximating structure during a procedure to effect optimal positioning of the tissue approximating structure and of the tissue.

Embodiments of anastomosis devices of the invention, in addition to the tissue approximating structure, can include features and structures that function to drain the bladder, e.g., through a drain lumen, while at the same time functioning as a tissue approximating structure that causes contact between severed tissue to allow the severed tissues to heal together. Methods of the invention can use such an anastomosis device, including both a draining function and a tissue approximating function, to accomplish healing of the anastomosis, without sutures, and draining of the bladder, with the single anastomosis device and preferably without removing or replacing the device during or after the procedure until healing is complete. The anastomosis device can be installed during or after a radical prostate removal procedure, and can remain installed with the bladder-draining function and the tissue-approximating function in effect until the anastomosis is completely healed and the severed tissue, e.g., bladder and urethra, are re-connected. Thus, an advantage associated with inventive methods and devices can be that the anastomosis device performs dual functions when installed during and following an anastomosis procedure, of draining the bladder and functioning as a tissue approximating structure, at the same time.

Also advantageously, inventive methods and devices avoid the need to use sutures to connect severed tissue such as a bladder neck and urethral stump. The ability to avoid sutures provides very significant advantages of avoiding the potential for damage to surrounding tissues and nerves that can be caused by installation of sutures using a needle. Such damage can include, for example, damage to ureters at the bladder or damage to the sphincter or nerves located in the perineal floor. Damage to any of these tissues has the potential to cause incontinence or impotency. Additionally, installing sutures is a difficult and technique-sensitive process that must be performed in a confined space and that would be avoided if possible based on other alternatives. Thus, the invention offers the very significant advantage of eliminating the need to use sutures to re-attach severed tissues, and the attendant potential damage to those sensitive proximal tissues and nerves and the possibility of incontinence or impotency.

In another respect, the inventive methods and devices, by eliminating sutures, can significantly reduce the amount of time required to perform an anastomosis procedure. For example, the amount of time for suture installation can be in the range of from 20 to 30 minutes up to an hour, depending on the type of procedure. A suturing step of a retropubic procedure, for example, may take 20 or 30 minutes, or up to an hour for a laparoscopic procedure. This amount of time may be significantly reduced, according to the invention, due to the elimination of a suturing step. Reduced procedure time creates the attendant advantages of reduced patient time under anesthesia, which can reduce the costs and complications caused by anesthesia, as well as related general costs.

According to the present description, the term "distal end" refers to a portion of an anastomosis device that is inserted into a body during an anastomosis procedure and that then becomes located in the region of the bladder, urethra, urethral stump, and perineal wall. The term "proximal end" refers to a portion of an anastomosis device that is opposite from the distal end, including a portion that remains exterior to the body during use.

The terms "tissue approximating" and simply "approximating" refer to a process of bringing or holding body tissues in contact for healing. Examples include: the process of bringing severed surfaces of a bladder neck and a urethral stump, or two opposing severed urethral tissues, into contact for healing; and the process of holding severed surfaces of a bladder neck and a urethral stump, or two opposing severed urethral tissues, together for healing.

An aspect of the device relates to an anastomosis device comprising a hollow, elongate, flexible catheter body having a proximal end and a distal end; an inflatable balloon at the distal end; a drainage lumen connected to the distal end; and tissue approximating structure on the catheter body on a proximal side of the balloon at a location to contact severed tissue during an anastomosis procedure.

Another aspect of the invention relates to an anastomosis device comprising a hollow elongate flexible catheter body having a proximal end and a distal end; an inflatable balloon at the distal end and inflation means for inflating the balloon; drainage means connected to the distal end for draining urine from a bladder; and tissue approximating means on the catheter body on the proximal side of the balloon for holding severed tissue in contact for healing.

Another aspect of the invention relates to a method of performing urethral anastomosis. The method comprises inserting a portion of an anastomosis device into the urethra, the anastomosis device comprising tissue approximating structure and a distal end comprising a balloon; inflating the balloon in the bladder; and using the tissue approximating structure to hold severed tissue together. Preferably, the device further comprises drainage apertures for draining a bladder and the method comprises draining a bladder.

Yet another aspect of the invention relates to a method of performing a urethral anastomosis. The method comprises severing a urethra to leave opposing severed urethral tissues; inserting a distal end of an anastomosis device through the urethra and into the bladder, the anastomosis device comprising tissue approximating structure and a balloon; inflating the balloon inside of the bladder, and holding the opposing severed urethral tissues together in healing contact using the tissue approximating structure. Preferably, the device further comprises drainage apertures for draining a bladder and the method comprises draining a bladder.

BRIEF DESCRIPTION OF THE DRAWINGS

FIGS. 9b and 9c are close-up schematic illustrations of portions of FIGS. 9 and 9a, respectively.

All drawings are not to scale.

DETAILED DESCRIPTION

An anastomosis device useful according to the invention can be any anastomosis device that can be useful in the practice of an anastomosis method described herein, e.g., an anastomosis method associated with a radical prostatectomy. An example of a useful design, generally, is the type sometimes referred to as a Foley catheter that has been constructed to include modified features as also presented in the present description including tissue approximating structure.

An anastomosis device of the invention typically includes a hollow, elongate, flexible catheter body having a proximal end and a distal end. An inflatable balloon can be located near the distal end, and an inflation lumen for inflating the balloon can extend to the balloon along the catheter body, e.g., along a portion or all of the catheter body from the proximal end to the balloon. During use, the balloon can rest against the neck of the bladder to prevent urine from entering the neck and to prevent urine from contacting the anastomosis site. Urine at the anastomosis site has the potential to cause difficulties in healing or to cause a stricture, among other deleterious effects. With the balloon blocking the bladder neck during use, urine will pool in the bladder and can be drained from the bladder, for example, using one or more draining apertures at the distal end of the anastomosis device connected to a drainage lumen. A drainage lumen can extend from one or more drainage apertures near the distal end, e.g., from apertures at the distal end to a location that is at or near the proximal end. As a particular example, a port may be present at the proximal end to connect the drainage lumen to a urine collection device.

Overall, an anastomosis device can contain various lumens (e.g., for inflating a balloon, for drainage, for containing actuating mechanisms for tissue approximating structure, etc.) and actuating mechanisms running along at least a partial length of a catheter body. The mechanisms and lumens can be arranged in any useful configuration such as coaxially, side-by-side, or according to any other useful configuration. A lumen or a mechanism (e.g., actuating mechanism) that runs along at least a portion of the length of the catheter body may be diverted at the proximal end of the catheter body to a port that provides access to the lumen or mechanism during use, as is known.

Figure 1:
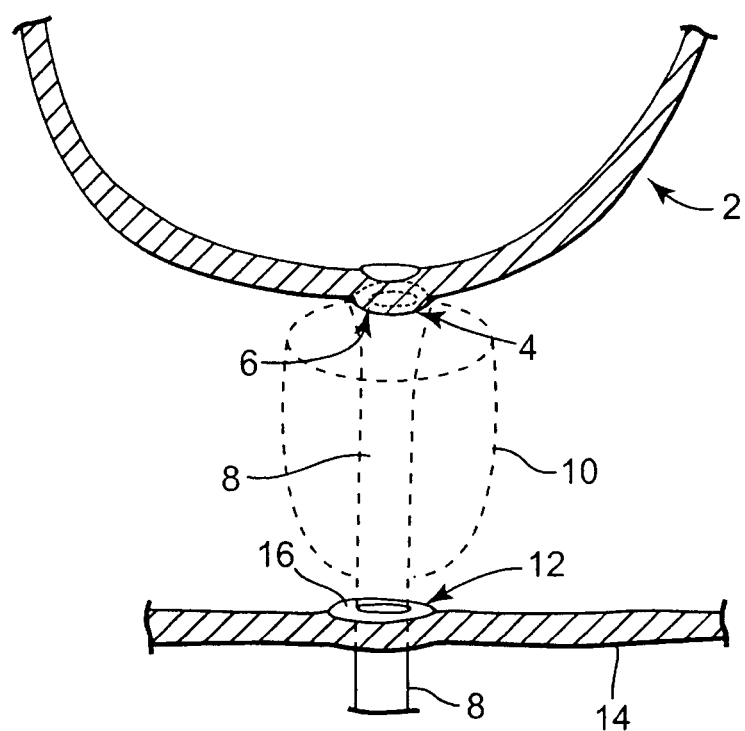
FIG. 1 is a schematic view to illustrate general aspects of radical prostate removal.
Figure 9:
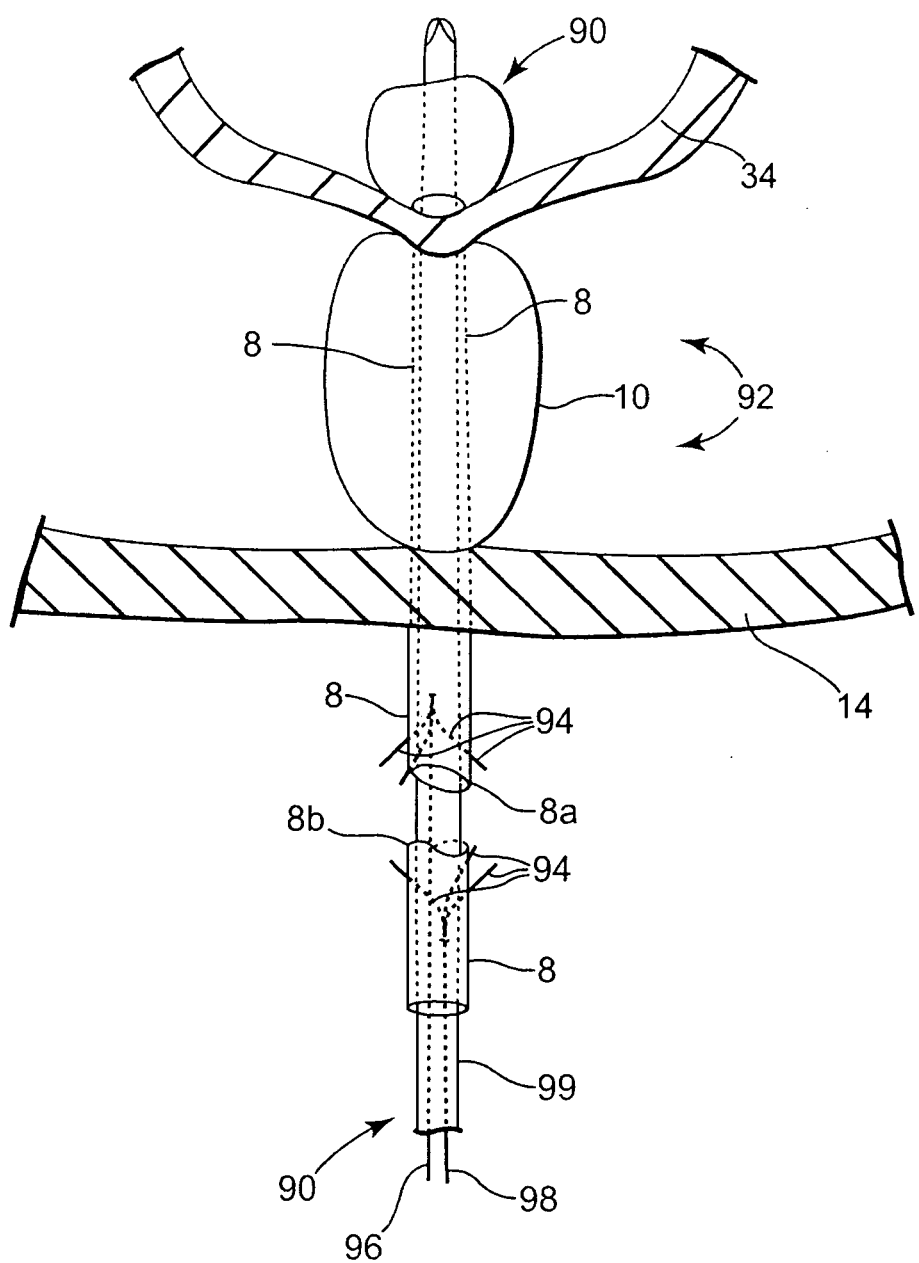
FIGS. 9, 9a, 9b, and 9c schematically illustrate an embodiment of an anastomosis device and a method of the invention.

According to the invention, the anastomosis device includes tissue approximating structure that can be used to place or hold a cut or severed tissue or tissue surface in place for healing while the catheter is installed. Referring to FIG. 1, a radical prostatectomy procedure includes removal of the prostate 10 (indicated in dashes) and urethra 8 (also in dashes), leaving bladder 2 with bladder neck 4 having a severed tissue surface 6 at one end of removed urethra 8, and a urethral stump 12 extending from perineal floor 14, with urethral stump 12 having severed tissue surface 16 opposing the severed surface 6 of bladder neck 4. Referring to FIG. 9, an end-to-end urethral anastomosis procedure includes a step of severing the urethra 8, below perineal wall 14, to leave two opposing severed urethral tissues 8a and 8b. While the following description presents inventive devices and methods primarily in the context of vesico-urethral anastomosis relating to radical prostatectomy, it will be apparent, and is also described, that the invention can be applied to a variety of other procedures that benefit from tissue approximating structures and in particular where a fluid flow is also desired, such as drainage of urine. A specific example is an end-to-end urethral anastomosis procedure.

A tissue approximating structure according to the invention can be a structure of the device that can be used to cause contact between severed tissues, such as severed urethral tissues, or such as severed tissue of the bladder or bladder neck with severed tissue of the urethral stump or perineal floor, or alternatively or additionally to hold severed tissue surfaces in contact with each other for healing. The tissue approximating structure may include, for example, one or multiple balloon or balloon-like structures that can be placed against the inside of the bladder or underneath the perineal floor to bring the severed bladder neck tissue into contact with the severed tissue surface of the urethral stump. Alternately, the tissue approximating structure may include elongate structures such as a needle, tine, prod, probe, or the like, which may have a blunt or a sharp end and may movably extend or protrude from an aperture in a flexible catheter body at a location where the structure can function as an approximating structure, e.g., at the distal end of the device where the structure will be near the bladder or perineal wall (when installed), or at a severed urethra below the perineal floor (when installed). Combinations of balloons and elongate structures may also be useful in certain applications. The tissue approximating structure does not require and can preferably exclude sutures and any component or structure designed to function in combination with a suture or suturing device such as a needle.

An example of a useful tissue approximating structure can be in the form of a sharp or blunt elongate structure (e.g., a sharp-ended needle or tine) that can be movably extended from an aperture at a distal end of, or at a length of, a catheter body, to thereby contact and optionally penetrate into or through one or more of a tissue of the bladder, bladder neck, urethra, bulbar urethra, urethral stump, or perineal floor, to place opposing severed tissue surface into contact for healing, and preferably also to hold the tissues in contact with each other during the healing period. Certain embodiments of the invention can include sharp or blunt elongate tissue approximating structure (e.g., a sharp-ended needle or tine) that can be movably extended from an aperture at a distal end of a catheter body to place opposing severed tissue of the bladder neck into contact with a severed tissue surface of the urethral stump, or vice versa, and preferably also to hold the tissues in contact with each other during the healing period.

Advantageously, in one embodiment, a tissue approximating structure may include one or more sharp elongate, straight or curved, fine metal tines that movably extend from the distal end of the catheter body at a location to allow contact and optionally penetration of the urethral stump proximal tissue in the adjacent perineal floor, urethra, or bulbar urethra. In this form, in addition to causing contact between the severed tissue surfaces of the urethral stump and the bladder neck, preferred elongate tissue approximating structure may also accomplish the desirable effect of re-exposing the urethral stump from the perineal floor by pressuring the urethral stump from below. As is common with vesico-urethral anastomosis procedures that include sutures, re-exposing the urethral stump after the urethra is severed can be useful because of the often very small amount of tissue associated with the urethral stump, and because of the tendency of the urethral stump to draw into the perineal floor.

As mentioned, certain preferred embodiments of tissue approximating structures can be movable, e.g., from a retracted or withdrawn position inside of the catheter body (e.g., for tines or needles) or a non-inflated position (for a balloon), to an employed or extended or otherwise "non-retracted" position. In the employed position, wherein the tissue approximating structure extends beyond the dimension (diameter) of the catheter body, e.g., as with a tine extending through an aperture in the catheter body wall, the tissue approximating structure can be positioned to contact a tissue and facilitate healing between a severed tissue and another severed tissue.

In general, a tissue approximating structure can include any structure that can be incorporated into or along the catheter body and can be manipulated, e.g., using a mechanism extending along the catheter body, to place or hold severed tissues in contact for healing. An anastomosis device according to the invention can have one or multiple tissue approximating structures, optionally multiple structures positioned at different distances along the length of the catheter body at one or more locations that allow the tissue approximating structures to contact and place pressure on opposing severed tissue surfaces when the anastomosis device is installed during an anastomosis procedure and afterward, for healing. For placing and holding severed bladder and urethral stump tissues, tissue approximating structure can be located at a suitable length along the catheter body, such as at the distal end where the tissue approximating structure will contact those tissues when installed. For placing and holding severed urethra tissue below the perineal wall, tissue approximating structure can be located further from the end of the device, at a suitable length along the catheter body to contact urethral tissue below the perineal wall when installed.

Exemplary tissue approximating structure may be in the form of a rigid elongate structure that moves from a retracted position (e.g., inside of the catheter body) to an extended position through apertures in the catheter body, such as a movable, elongate, tine or needle type structure. Such a tine or needle structure may include a pointed end to penetrate into or through a tissue. Exemplary elongate structures can be positioned to movably engage apertures in the catheter wall through which the elongate structures can be extended or retracted. Optionally, a guide such as a metal, ceramic, rigid plastic, or polymeric guide can be placed at the aperture between the catheter body wall and the movable elongate structure.

Alternatively, the tissue approximating structure may include one or two balloons that can be positioned to cause contact of two opposing severed tissue surfaces. For example, two balloons may be located to contact the opposite sides of a bladder wall and a perineal floor, one balloon in the bladder and the other below the perineal floor, at a spacing that maintains contact between a severed bladder neck tissue and a severed urethral stump.

In certain preferred embodiments, a tissue approximating structure may comprise multiple, (optionally) opposing sets of elongated structures such as rigid or semi-rigid tines, needles, or the like, which may be straight or curved, and which may optionally include a sharp pointed tip to penetrate into or through a bladder neck, bladder wall, perineal floor, urethra tissue, bulbar urethra, urethral stump, or any other tissue that can be brought into contact or held together by devices or methods described herein. For example, one or a set of tines may be located at positions along the catheter body where tissue approximating structure can be used to contact severed tissue or tissue proximal to severed tissue, to bring together and hold in place severed tissue for healing with a corresponding severed tissue. As one specific example, an anastomosis device according to the invention may include multiple sets of elongate tissue approximating structures including a first set of movable distal tissue approximating structures positioned to extend through apertures in the hollow catheter body, the distal tissue approximating structure located on the proximal side of the balloon, and a second set of movable proximal tissue approximating structure positioned to extend through apertures in the hollow catheter body, the proximal tissue approximating structure located on the proximal side of the movable distal tissue approximating structure. Each tine or set of tines can be extended independently and remotely, for example by operation of an actuating mechanism such as connected wire or shaft that runs through or along the length of the catheter body.

Figure 2:
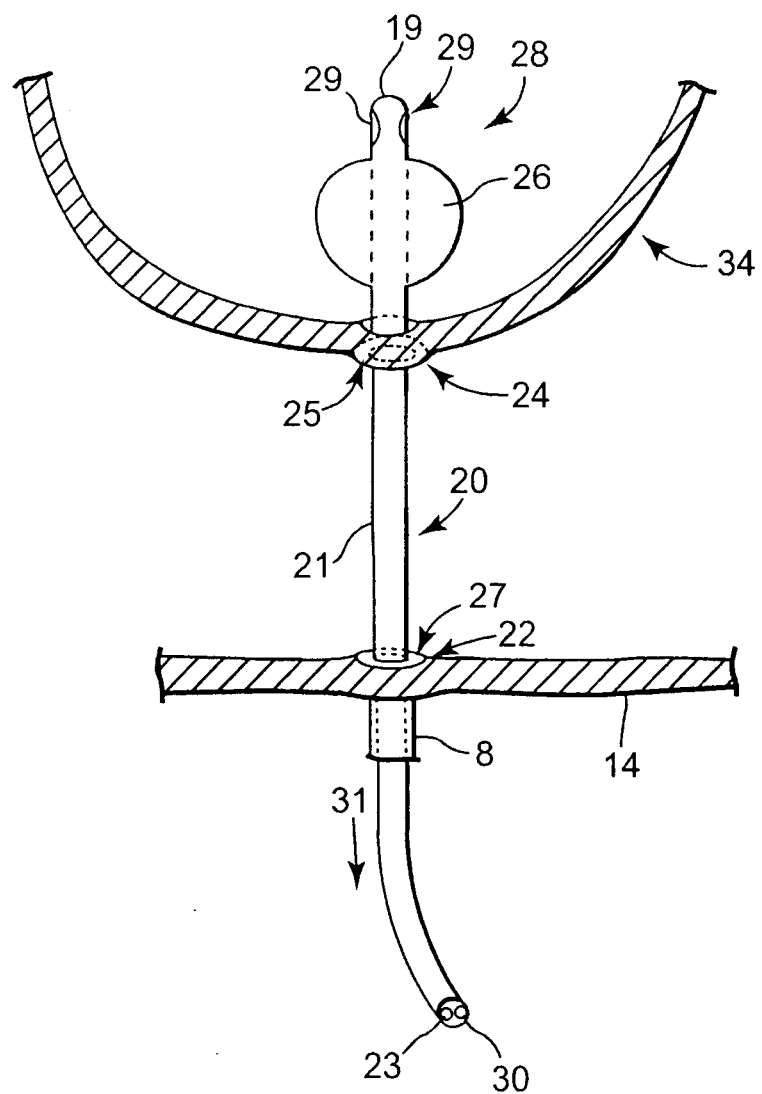
FIGS. 2 and 2a schematically illustrate an embodiment of anastomosis devices according to the invention.
Figure 2A:
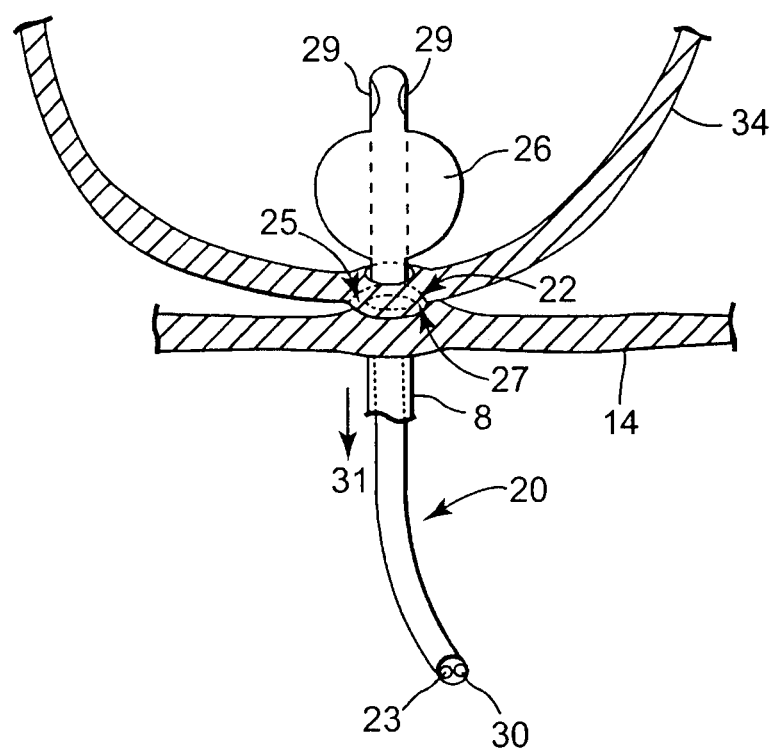

According to certain presently preferred embodiments of the invention, a tissue approximating structure may comprise a balloon located at the distal end of the device, the balloon being positioned inside of the bladder during use. FIGS. 2 and 2a illustrate such an embodiment of an anastomosis device of the invention, installed for use within urethra 8 and bladder 34 following removal of a prostate (not shown).

Referring to FIG. 2, a prostate has been removed to leave a severed urethral stump tissue 22 and opposing severed bladder neck 24. Anastomosis device 20 is installed through urethral stump 22 and bladder neck 24. The device 20 comprises a catheter body 21 and balloon 26 located at the distal end 28 of the device. Preferably and as shown, the device also includes drain lumen 23 and drain apertures 29 located between the tip 25 of the distal end of the device 20 and balloon 26. Balloon 26 is inflated, after insertion into the bladder 34, by a flow of fluid through balloon lumen 30. Pressure (e.g., traction as shown by arrow 31) can then be applied through the length of device 20 to produce a pressure against the inside of bladder 34 from inflated balloon 26. Referring to FIG. 2a, balloon 26 can be brought to place pressure on the interior of the bladder 34 and draw the severed bladder neck tissue 25 into contact with severed urethral stump tissue 27. The surface of severed bladder neck tissue 25 aligns automatically with the surface 27 of severed urethral stump 22, around and along the axis of the catheter body 21, provided that no gap exists between the surfaces 25 and 27 of the respective severed tissues.

Figure 3:
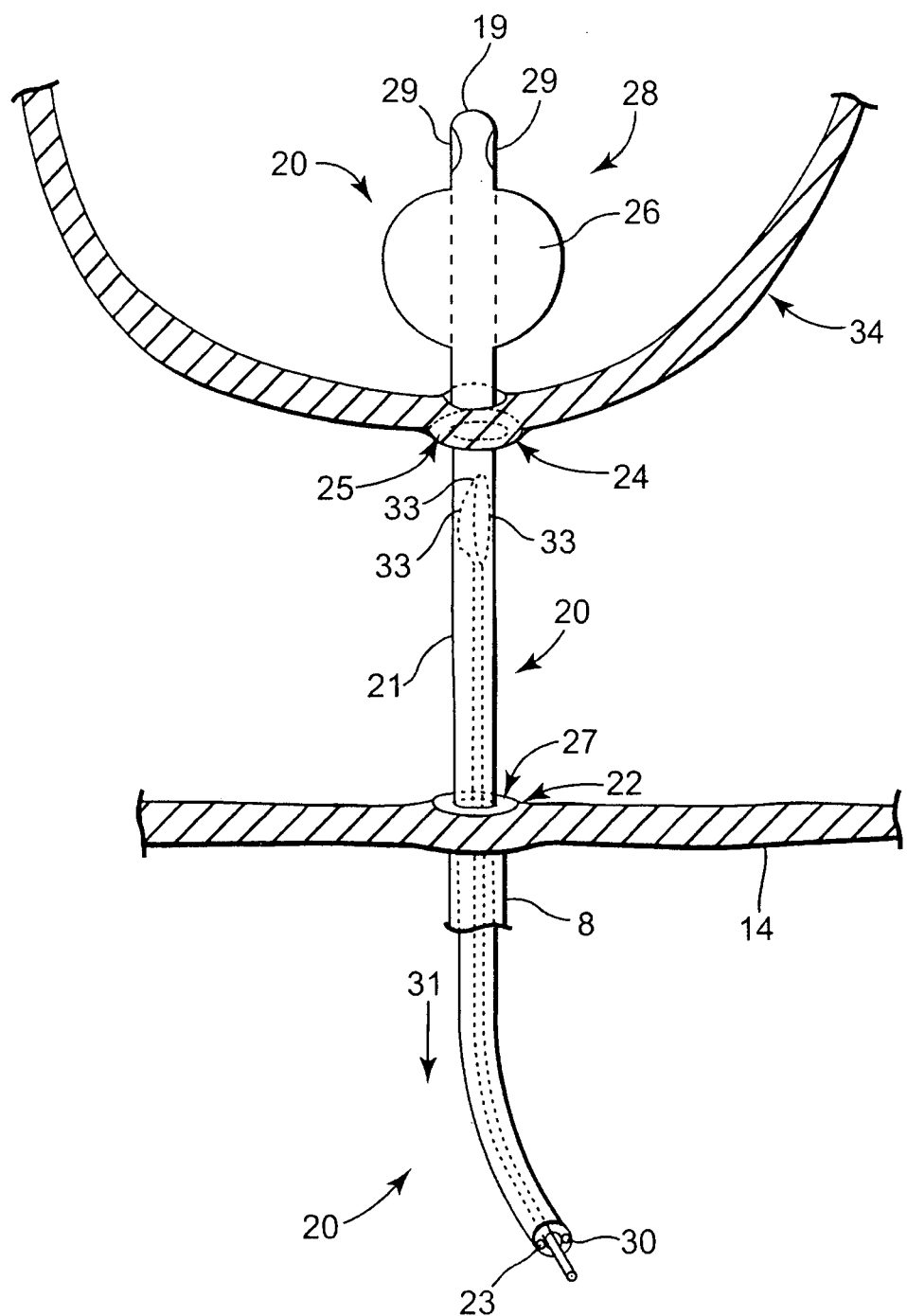
FIGS. 3 and 3a schematically illustrate an embodiment of anastomosis devices according to the invention.

In related embodiments of devices according to FIGS. 2 and 2a, the anastomosis device 20, which in FIGS. 2 and 2a uses balloon 26 as a tissue approximating structure, may optionally and preferably include additional components or features as part of the tissue approximating structure. As an example, FIG. 3 shows how additional tissue approximating structure may be located along the length of the catheter body 21, at a location that will place the structure at or below the urethral stump 22 or the perineal floor 31. Such additional tissue approximating structures may be in the form of one or preferably multiple elongate metal tines 33 (three are shown, in the retroacted position) having sharp ends to penetrate into the urethral stump, perineal wall bladder tissue urethral tissue, or other location that is useful to draw or hold together severed tissue. Located to exit the catheter body 21 through apertures (not shown) to contact tissue at or proximal to the urethral stump 22 or perineal floor 31, the tines 29 may extend from the catheter body 21 at a position (when installed, with the bladder drawn down to the perineal floor) below or proximal to the urethral stump 22 or perineal floor. By extending from an aperture at that location, the tines (or another form of tissue approximating structure) may produce pressure against the urethral stump 22 in a direction that pushes the urethral stump toward bladder neck 24.

Figure 3A:
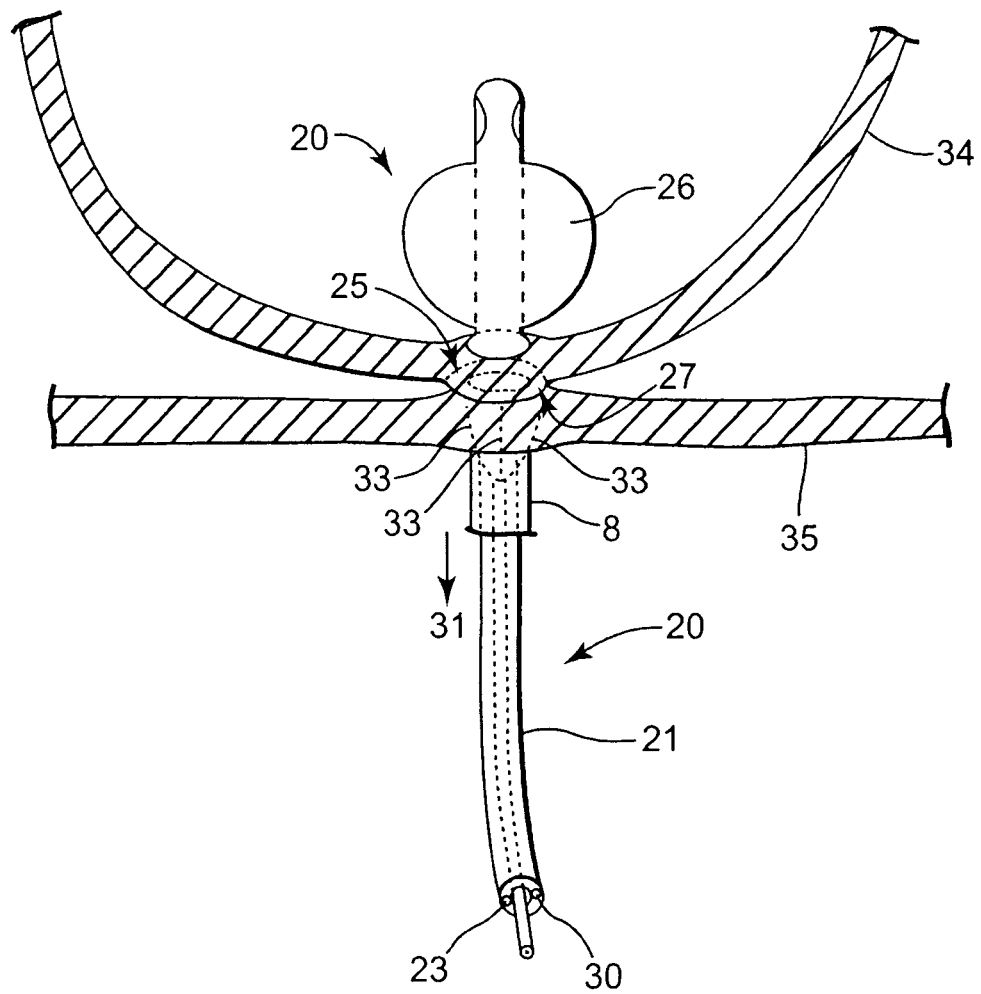

Referring still to FIG. 3, the prostate (not shown) has been removed to leave a severed urethral stump tissue 22 and opposing severed bladder neck 24. Anastomosis device 20 is installed through urethra 8, urethral stump 22, and bladder neck 24. The device 20 comprises balloon 26 located at the distal end 28 of the device. Preferably and as shown, the device also includes drain lumen 23 and drain apertures 29. Balloon 26 is inflated and pressure (e.g., traction 31) is applied through the length of device 20 to produce a pressure against the inside of bladder 34 (see FIG. 3a) from inflated balloon 26 to place the severed bladder neck tissue 25 in contact with severed urethral stump tissue 27. As shown in FIG. 3a, the surface 25 of the severed bladder neck aligns automatically with the surface 27 of the severed urethral stump, around and along the axis of the catheter body 21. Also shown in FIG. 3a are tines 33 that extend from catheter body 21 at a position below perineal floor 35 and penetrate into perineal floor 35 (optionally contacting or penetrating tissue below the perineal floor 35 such as the bulbar urethra, which is not shown, or urethra 8). The severed urethral stump tissue 27 is pushed against the severed surface 25 of the bladder neck to allow healing together and reconnection of the two severed tissue surfaces.

Figure 4:
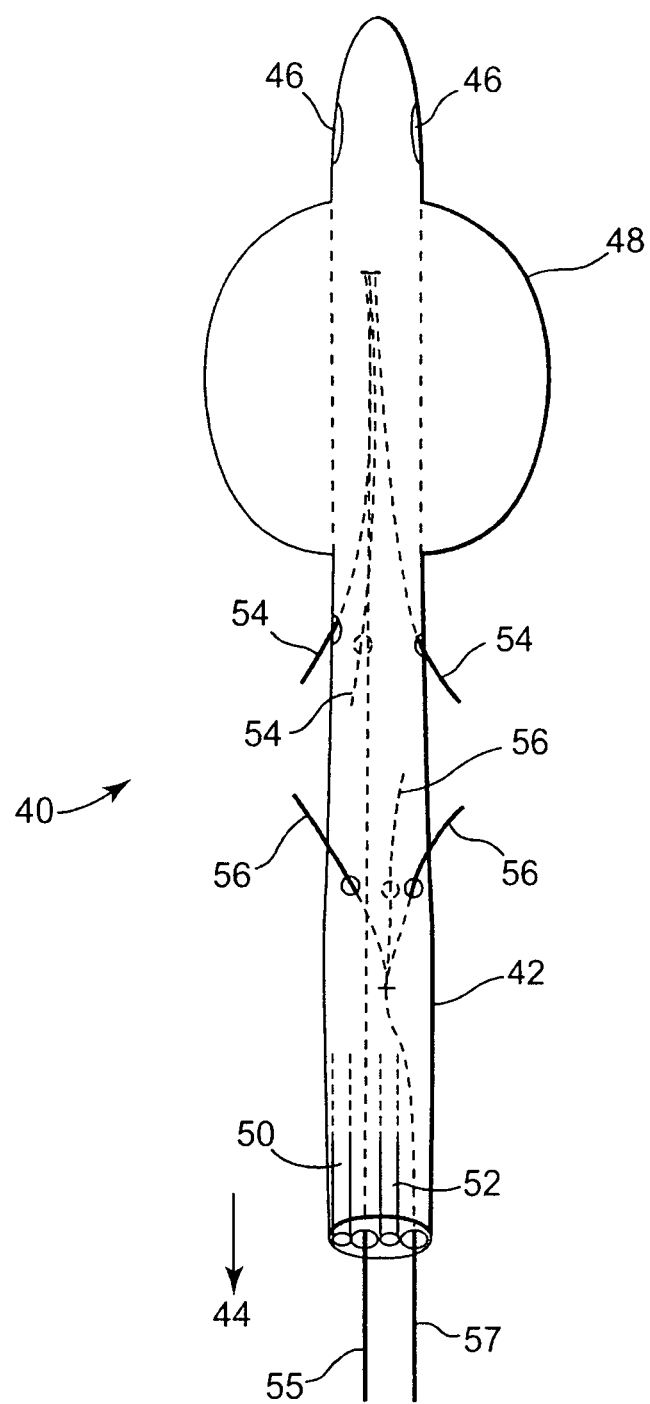
FIGS. 4 and 4a schematically illustrate an embodiment of anastomosis devices according to the invention.

FIG. 4 shows another example of a distal end of an approximating device of the invention. Distal end 40 includes a catheter body 42 with a proximal end 44 (not shown). The device includes a balloon 48, an inflation lumen 50 (partially shown), and a drainage lumen 52 (partially shown). Inflation lumen 50 extends within the catheter body 42 from the proximal end to the balloon 48, in fluid communication with the balloon 48, for inflating and deflating the balloon 48. The drainage lumen 52 extends from the proximal end 44 to the distal end 40 and to drainage apertures 46. One set of tines 54 is located on the distal end 40 of the device, retractably extending through catheter body 42, proximal to balloon 48. Tines 54 movably extend through apertures (not numbered) and in the general direction back toward the proximal end of the catheter body and away from the distal end. Another set of tines 56 is located at the distal end 40 of the device 40, but toward the proximal end of the device relative to balloon 48 and also toward the proximal end of the device relative to tines 54. Tines 56 movably extend through apertures (not numbered) and in the direction toward the distal end of the catheter body and away from the proximal end. Each set of tines 54 and 56 can be independently remotely operated, e.g., by using actuating connections 55 and 57 that extend through the catheter body 42 to the proximal end.

In use, when anastomosis device 40 of FIG. 4 is installed, balloon 48 is located inside of the bladder and tines 54 can be positioned at a position along the catheter body 42 so that when extended from the body 42, tines 54 penetrate into tissue for placing and preferably holding a severed tissue in place next to a corresponding severed tissue. As a specific example, tines 54 and 56 can be positioned along the catheter body 42 so that when extended from the body 42 during use, tines 54 penetrate into tissue of the bladder and tines 56 penetrate into tissue of the perineal floor, the opposing tines applying pressure to hold the severed urethral stump against the bladder neck.

Figure 5:
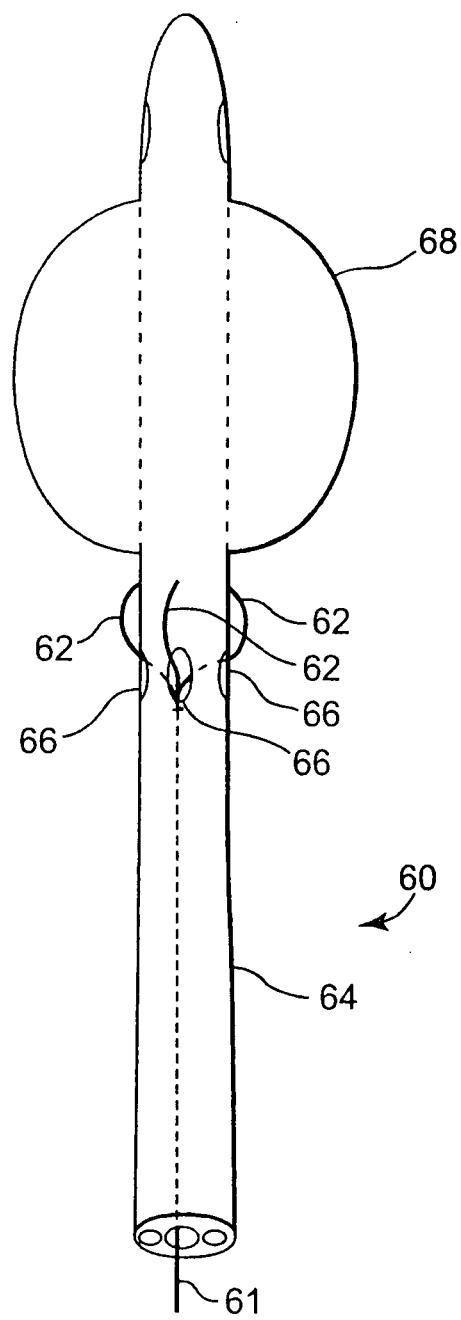
FIGS. 5 and 5a schematically illustrate an embodiment of anastomosis devices according to the invention.

Still another embodiment of an anastomosis device of the invention can have a single set of elongate tissue approximating structures, e.g., curved tines, that extend from a single position (i.e., a common distance from an end) along the length of a catheter body. The tissue approximating structure may extend through apertures and from the catheter body to contact a tissue, e.g., penetrating into the tissue and optionally through the tissue. An example is shown in FIG. 5. FIG. 5 illustrates a distal end 60 of an exemplary anastomosis device of the invention, containing a single set of three curved tines 62. In use, when the anastomosis device having distal end 60 is installed, balloon 68 is located inside of a bladder and tines 62 can, for example, be positioned at a position along the catheter body 64 to extend from the catheter body 64 to penetrate first into and through tissue of the perineal floor, then into the bladder wall (see FIG. 5*a*). As a result, the single set of tines 62 can be effective to hold a severed bladder tissue in place next to a severed urethral stump. Tines 62 can be extended or retracted through apertures 66 in catheter body 64, using actuator 61. In this embodiment, the actuator 61 runs through a lumen along the length of catheter body 64 and splits into or connects to the three individual tines 62, which exit the catheter body 64 through apertures 66.

Figure 6:
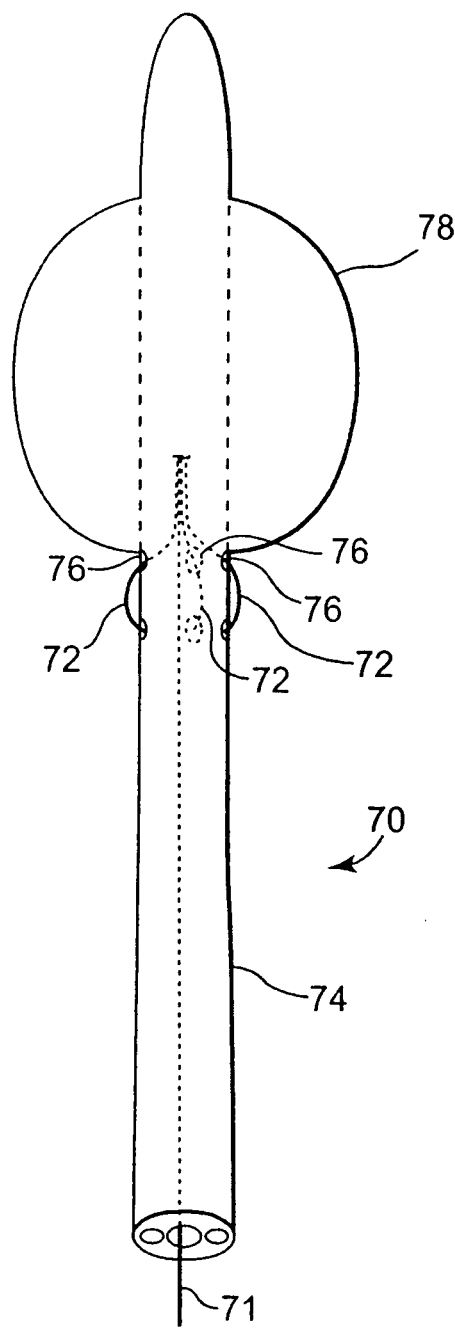
FIGS. 6 and 6a schematically illustrate an embodiment of anastomosis devices according to the invention.

An alternative embodiment of anastomosis device could include a single set of tines that extend from the anastomosis device in the opposite direction from that shown in FIG. 5. Such an embodiment is shown in FIG. 6. FIG. 6 illustrates an example of a distal end 70 of an anastomosis device according to the invention, containing a single set of curved tines 72. In use, balloon 78 is located inside of a bladder, and tines 72 can be positioned, for example, along the catheter body 74 to extend from the catheter body 72 to penetrate first into and through tissue of the bladder, then into and through the perineal floor (see FIG. 6*a*). Tines 72 can be extended or retracted through apertures 76 in catheter body 74 using actuator 71. In this embodiment, the actuator 71 runs through a lumen along the length of catheter body 74 and splits into or connects to the three individual tines, which exit catheter body 74 through apertures 76.

Alternate embodiments of anastomosis devices (and related methods) will be useful according to this description, as will be appreciated by those of skill, even if not specifically illustrated or described. For example, combinations of the above described features of an anastomosis device, as well as other features such as additional or different structures or protrusions, can be useful to function as tissue approximating structures. Examples may include a second balloon (see, e.g., FIG. 7) or other movable, inflatable, or stationary structures. Additionally, the number or structure of the tissue approximating structure (e.g., tines) may be of any useful variation, as may be the mechanism by which a tissue approximating structure is actuated.

The catheter and its componentry may be made of materials normally used and known to be useful for such devices, or future developed materials, especially including known or future developed materials that are relatively inert and biocompatible. For example, a catheter body may be prepared from a flexible plastic or polymeric material. Examples of presently understood materials that may be useful for a catheter body can include silicones, latex, rubbers, polyurethanes, and combinations of these or other materials. A tissue approximating structure can be made from these or other materials, including relatively rigid plastics, polymers, or metals, optionally including bioresorbable materials such as bioresorbable polymers. Examples of metals include stainless steel, nitinol, titanium, tantalum, as well as alloys or combinations of these materials.

Optionally, portions or all of an elongate tissue approximating structure may be bioresorbable, if desired. This could allow for devices and methods that allow the bioresorbable structure (e.g., a bioresorbable tine) to remain in place after removal of the anastomosis device, after which the bioresorbable structure would resorb over time.

The tissue approximating structure can be actuated by any useful method or device or structure, for example as illustrated in the attached figures, by an elongate actuator mechanism extending through a lumen in a catheter body. The actuator mechanism may be of the same material as the tissue approximating structure, or may be a different material secured to the tissue approximating structure. The actuator may extend out of the proximal end of a device or may enter the device through a lateral port located at the proximal end of the device.

The device, in addition to the foregoing, may also include other mechanisms or features, as will be appreciated by those of skill. Examples include features such as a temperature probe or temperature reading mechanism. As one example of a specific feature that may be incorporated into a preferred embodiment of the invention, an actuator mechanism for a tissue approximating structure may be removable at an exterior portion of the device. For example, an actuator mechanism may extend through a catheter body through an end or through a port at the proximal end of the device. The actuator mechanism or a portion thereof may be removably attached to the device and the tissue approximating structure, so that the surgeon can operate the tissue approximating structure while the actuator mechanism is attached during a surgical procedure, and the actuator may be removed following the procedure to avoid inadvertent actuation by the patient during the healing period, during which the device is still installed in the patient. When the time comes to remove the device, the actuator mechanism may be re-attached externally to uninstall the device.

In general, a catheter can be used during urethral anastomosis procedures such as that associated with a radical prostatectomy, e.g., vesico-urethral anastomosis, with the catheter functioning to remove urine from the bladder after the procedure. By ordinary methods, and according to the inventive methods described herein, an anastomosis device can be used by inserting the elongate flexible catheter body through the urethra and into the bladder. A portion of the distal end of the device becomes located inside of the bladder where the balloon can be inflated and where the drainage lumen can be used to drain the bladder and keep urine out of the bladder during and subsequent to the procedure. The bladder can preferably be drained of urine during the procedure and during the healing period following the procedure, because urine is preferably kept away from the site of anastomosis to facilitate healing, and also to prevent urine from creating pressure within the bladder.

A typical Foley catheter can include a drainage lumen and an inflation lumen for inflating and deflating the balloon. The balloon is normally deflated until properly positioned in a patient's bladder. Once the catheter is properly positioned, the inflation lumen delivers fluid to inflate the balloon. The inflated balloon can be used to hold the catheter in place, and, in embodiments of the invention, can also be used to draw the bladder and bladder neck toward the urethral stump and to hold the bladder in that position during healing of the bladder neck to urethral stump. Inventive devices and methods additionally allow for the use of other tissue approximating structures, such as tines, needles, probes, prods, balloons, etc., or combinations of these and other structures, to place severed tissue into contact and hold the tissues together for healing.

Figure 8:
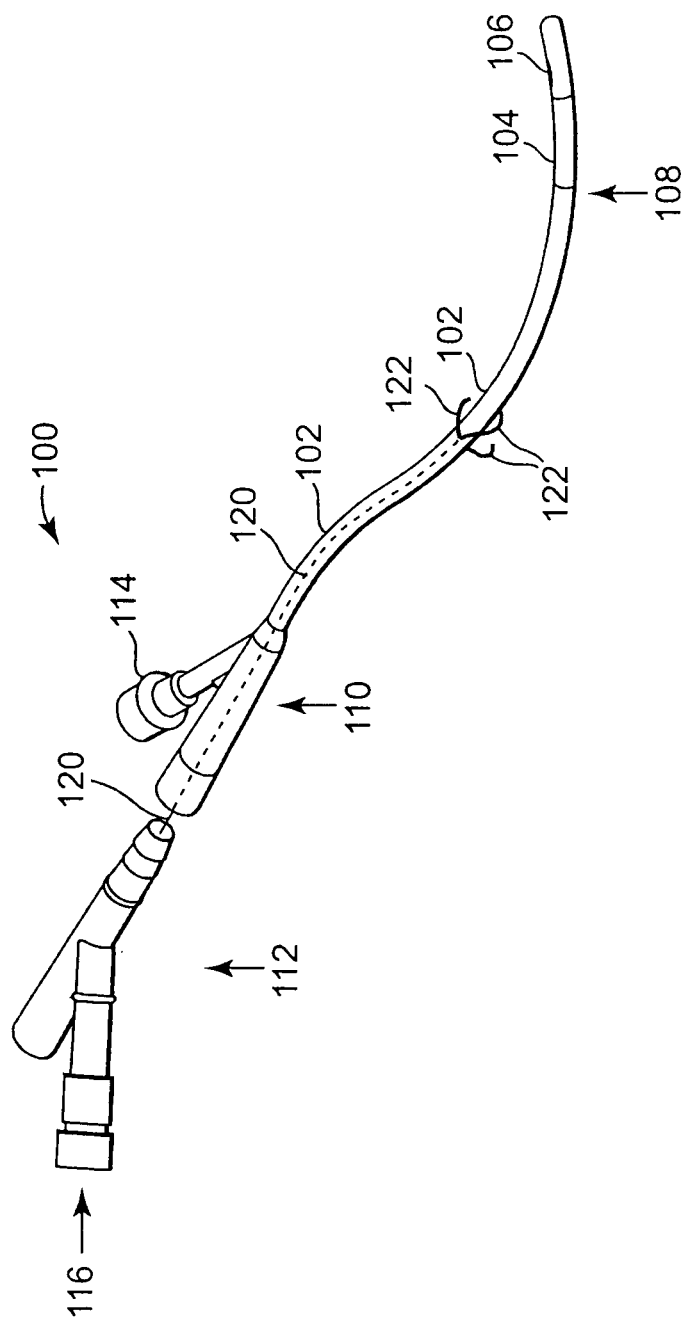
FIG. 8 schematically illustrates an embodiment of an anastomosis device of the invention.

FIG. 8 shows a single example of a modified-Foley-catheter-type anastomosis device according to the invention. Device 100 includes distal end 108, catheter body 102, balloon 104, and drainage aperture 106. Tissue approximating structure can be located along the catheter body 102, for example, as illustrated, along catheter body 102 approximately midway between the far ends of the device. (This location may be useful, for example, in performing an end-to-end urethral anastomosis procedure; a location closer to balloon 104 may be useful for a vesico-urethral anastomosis). Tissue approximating structure of device 100 is shown as a single set of tines 122 (shown in an extended position) but may alternatively include an additional set of (optionally opposing) tines, a different type of elongate structure such as a probe or prod or needle, a balloon, or any other structure that may be used to place or hold severed tissue in contact with another opposing severed tissue for healing.

Still referring to FIG. 8, device 100 includes proximal end 110 that includes a port 114 and that can be connected to attachment 112. Useful such proximal end and attachment configurations are well known, and such known or future developed proximal ends and attachments will be understood to be useful according to devices and methods of the invention. In the illustrated embodiment, proximal end 110 includes a port 114 that may connect to a lumen (not shown) such as an inflation lumen for balloon 104 or a drainage lumen from aperture 106. Another port, 116, part of attachment 112, can also be used with an inflation lumen or a drainage lumen. Connector 120 is part of an actuating mechanism for extending and retracting tines 122. Connector 120 may be attached to another portion of an actuating mechanism such as a turnable knob or a lever (not shown), etc., that can be moved or rotated to extend or retract tines 122. Other variations of these features of the illustrated attachment and proximal end will be understood by those of skill, and may be used in combination with the features of the present invention.

Generally, a method of the invention can include a step of performing a radical prostatectomy by a known or future developed technique, such as by a retropubic technique, a laparoscopic technique, or a transperineal technique. These techniques leave a bladder neck and a urethral stump for re-attachment. Prior techniques may use sutures or other mechanisms or structures that are separate from a catheter to re-attach the severed tissue. The use of sutures or other such separate mechanisms or structures is preferably not necessary and most preferably avoided according to methods of the invention.

The distal end of the anastomosis device may optionally be partially installed during the prostatectomy procedure, e.g., up to the perineal floor, or may be installed to that point afterward. Following removal of the prostate, the catheter body of the distal end of the device is passed through the urethral stump and then through the bladder neck. From there, the technique can include inflating the balloon inside of the bladder, and using tissue approximating structure to place the severed tissue surfaces of the urethral stump and the bladder neck into contact for healing. A preferred step can also be to close the bladder neck to a desired size via a purse-string suture.

From this point, the steps and techniques used to actuate the tissue approximating structure and place the severed urethral stump and bladder neck tissue into contact for healing, can depend on factors that include the structure and actuating mechanisms associated with the particular anastomosis device that is used.

Common to all vesico-urethral techniques can preferably be to carefully avoid damaging sensitive tissues near the bladder neck and urethral stump. Specifically, ureters are proximal to the bladder neck and should not be contacted. Proximal to the urethral stump are sensitive nerves and a sphincter. Some of these tissue structures are generally regarded as being at the 5 o'clock and 7 o'clock positions of the bladder neck and the urethral stump. Advantageously, the devices and methods of the invention can afford significant opportunity to identify the location of these tissues, and position and re-position the tissue approximating structures to avoid them. As an additional feature of the device, markings can be made along a length of the outer surface of the catheter body, e.g., at the location of apertures from which elongate tissue approximating structures extend. A surgeon can view these markings when positioning the catheter body relative to a urethral stump and bladder neck, to avoid potential damage to sensitive tissue locations. Also in preferred embodiments, elongate tissue approximating structures such as tines or needles can be constructed and located to facilitate avoidance of sensitive tissues, such as by providing a set of three tines that radiate from a cross section of a catheter body at approximately 120 degree angles apart from each other.

Figure 7:
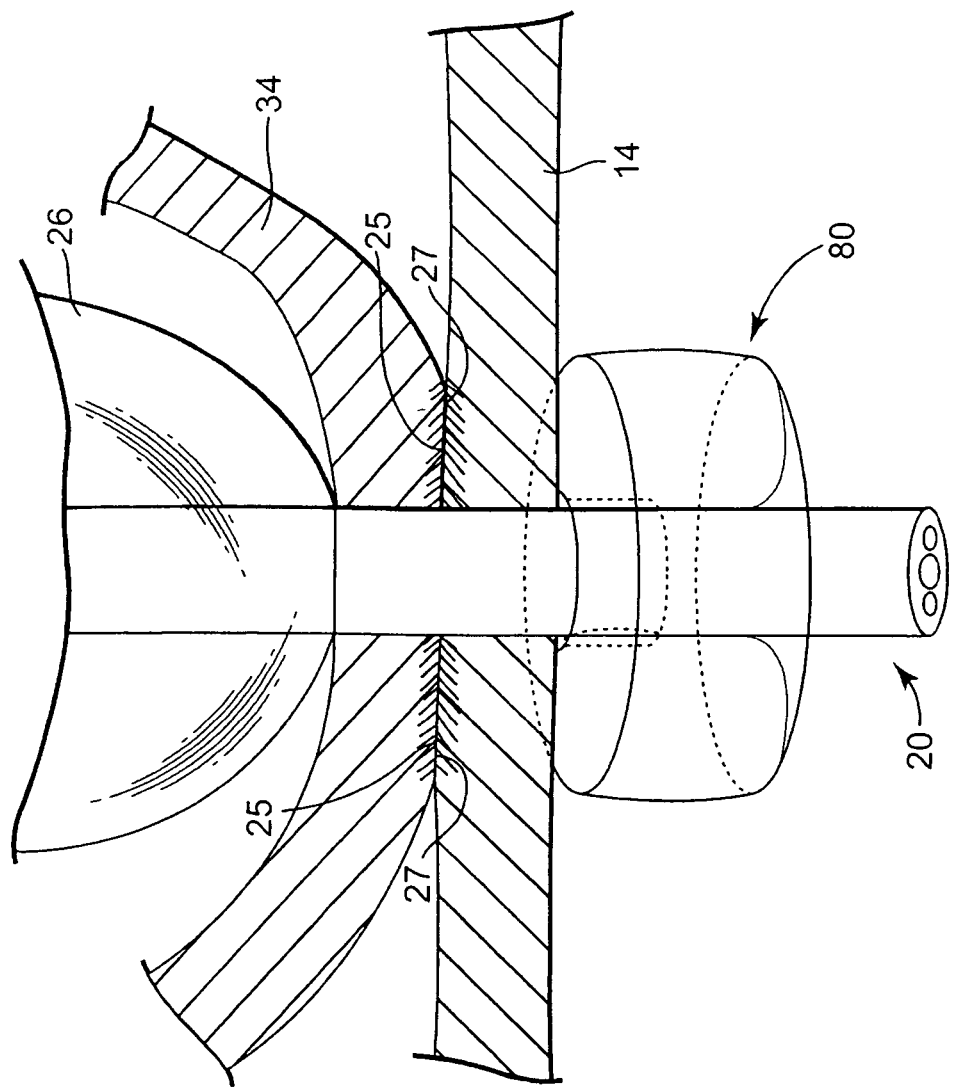
FIG. 7 schematically illustrates an embodiment of anastomosis devices according to the invention.

Examples of steps to install tissue approximating structures can be described by reference to the figures. Referring to FIGS. 2 and 2a, an example of steps for using the tissue approximating structure of the illustrated embodiment of the anastomosis device shown, can be as follows. Following inflation of balloon 26 inside of bladder 34, the bladder is pulled against perineal wall 14 (see FIG. 2a). Severed bladder neck surface 25 contacts severed urethral stump tissue 27, to allow healing with the device 20 installed. Optionally and preferably, another form of tissue approximating structure may be employed proximal to the perineal floor 14 to produce pressure from the perineal floor 14 against the bladder neck 24 and balloon 26. The additional form of tissue approximating structure may be in the form of a second balloon, or one or more elongate structures extending from the catheter body 21, through apertures, from underneath or at the level of the perineal wall 14. FIG. 7, for example, shows a second balloon 80, which applies pressure to perineal floor 14, from below.

Figure 4A:
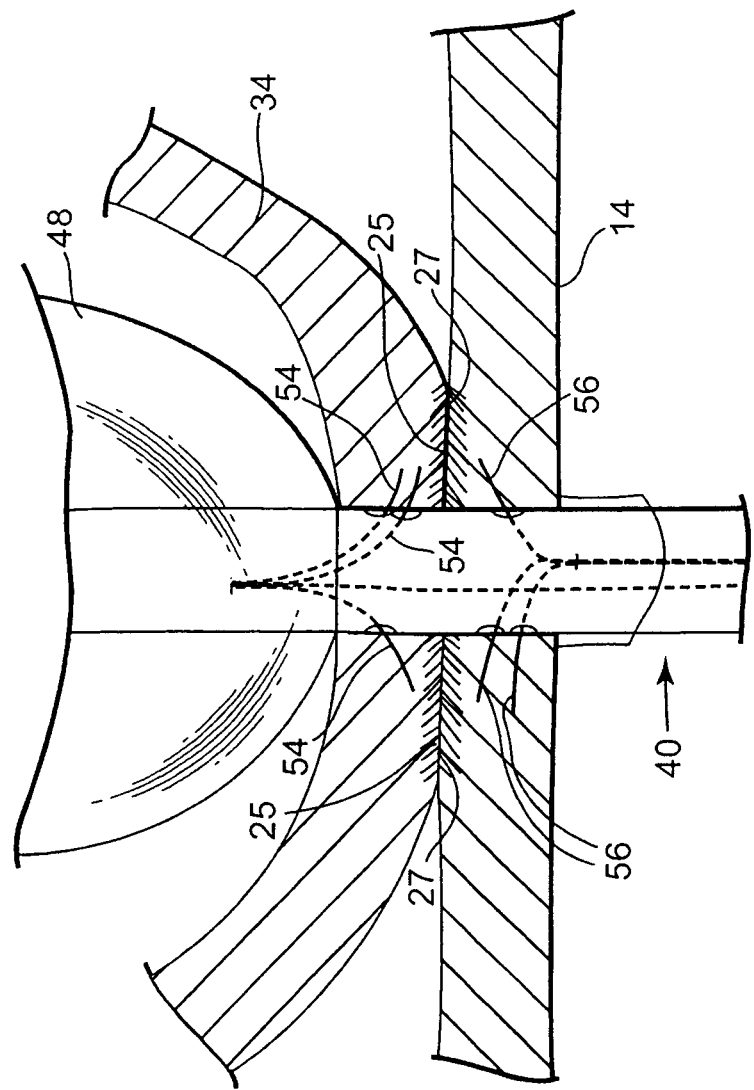

As another example, referring to FIG. 4a, following inflation of balloon 48 inside of bladder 34, the bladder is pulled against perineal wall 14. Severed bladder neck surface 25 contacts severed urethral stump tissue 27. Prior to or after pulling the bladder 34 to contact the perineal wall 14, a distal approximating structure in the form of tines 54 are extended from catheter body 40 and penetrate bladder tissue 34, carefully avoiding ureters (not shown) optionally by reviewing the position of tines 54 and repositioning or re-inserting the tines as necessary either by retraction of the tines or by adjusting the position of the catheter body 40 relative to the bladder tissue 34. Tines 54 may penetrate into or through bladder tissue 34, as desired. After pulling the bladder to contact the perineal wall 14, proximal tissue approximating structure in the form of tines 56 are extended from catheter body 40 to penetrate perineal wall 14. Again, sensitive tissue is carefully avoided with optionally review and re-positioning of tines. Severed bladder neck surface 25 contacts severed urethral stump tissue 27, to hold the severed tissue surfaces together to allow healing, while the anastomosis remains installed. Upon completion of the healing process, tines 54 and 56 are retracted back into the catheter body 40, and the device can be removed.

Figure 5A:
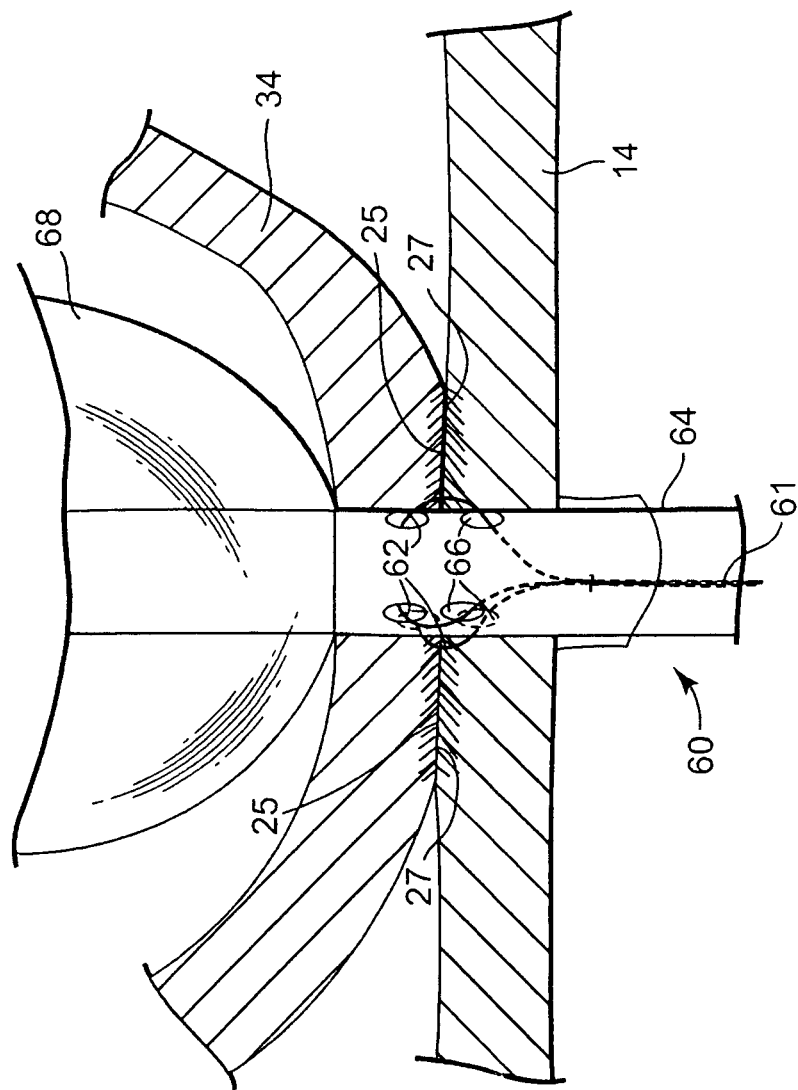

As still another example, referring to FIG. 5a, following inflation of balloon 68 inside of bladder 34, the bladder is pulled against perineal wall 14. Severed bladder neck surface 25 contacts severed urethral stump tissue 27. Tissue approximating structure in the form of tines 62, proximal to the perineal floor 14 can be extended to penetrate into and through perineal floor 14, and then further penetrate into bladder tissue 34. Severed bladder neck surface 25 contacts severed urethral stump tissue 27, to allow healing, while the anastomosis remains installed. Upon completion of the healing process, tines 62 are retracted back into the catheter body 64, by use of actuator 61, and the device can be removed.

Figure 6A:
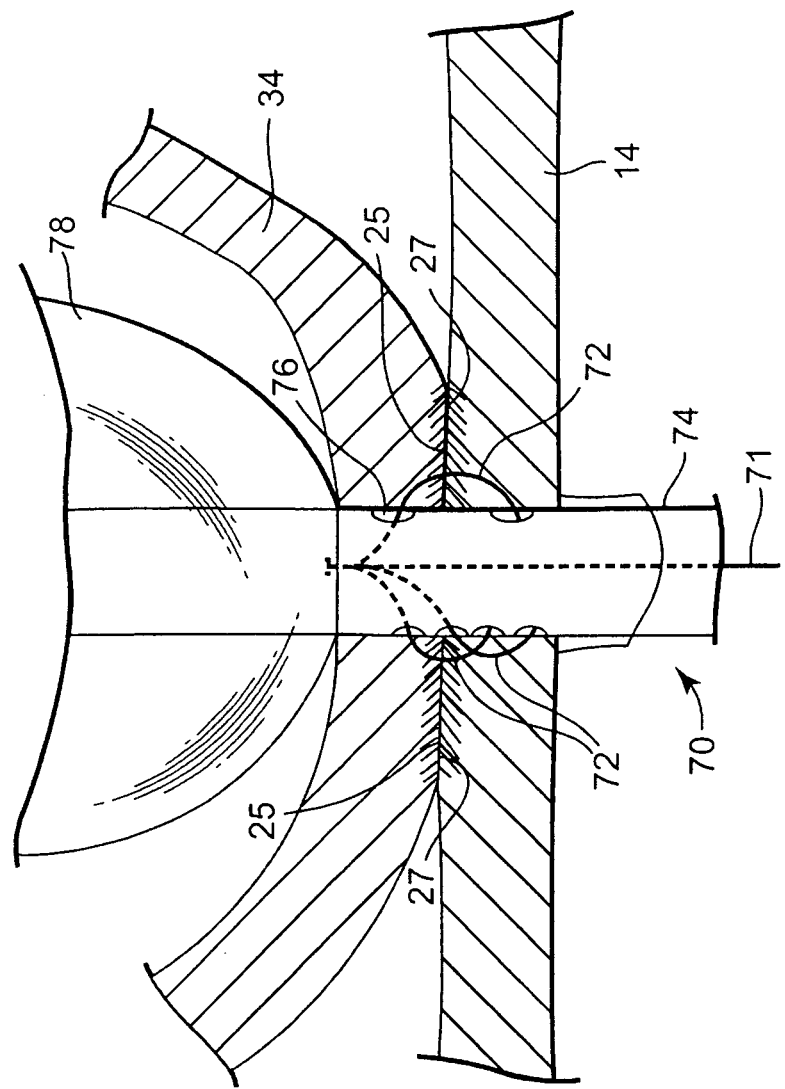

FIG. 6a shows steps of another embodiment of a method and device of the invention. Following inflation of balloon 78 inside of bladder 34, the bladder 34 is pulled against perineal wall 14. Severed bladder neck surface 25 contacts severed urethral stump tissue 27. Tissue approximating structure in the form of tines 72, proximal to bladder tissue 34 can be extended to penetrate into and through bladder tissue 34, and then further penetrate into perineal floor 14. Severed bladder neck surface 25 contacts severed urethral stump tissue 27, to allow healing, while the anastomosis remains installed. Upon completion of the healing process, tines 72 are retracted back into the catheter body 74, and the device can be removed.

FIG. 9 shows still additional embodiments of inventive methods and devices relating to a urethral anastomosis procedure below the perineal floor. FIG. 9 illustrates device 90 having distal end 92 installed through perineal floor 14 and into bladder 34, through urethra 8 which passes through prostate 10. This procedure does not include removal of the prostate, but instead relates to severing and re-attaching urethra 8 at a point below perineal wall 14, e.g., re-attaching severed urethra portions 8a and 8b. According to the illustration, three tines 94 can be used to place surfaces of severed urethra portions 8a and 8b together, and hold them together for healing (see FIG. 9a). Specifically, tines 94, total six tines, three as a distal set of tines pointed approximately away from the distal end of the device and three as a proximal set of tines pointed approximately toward the distal end of the device. Each set, the distal set and the proximal set, is independently movable by actuating mechanisms 96 and 98 to retract or extend through apertures in catheter body 99. When installed, tines 94 are located along the catheter body 99 at a location that allows each set to contact a severed urethra tissue portion.

Figure 9A:
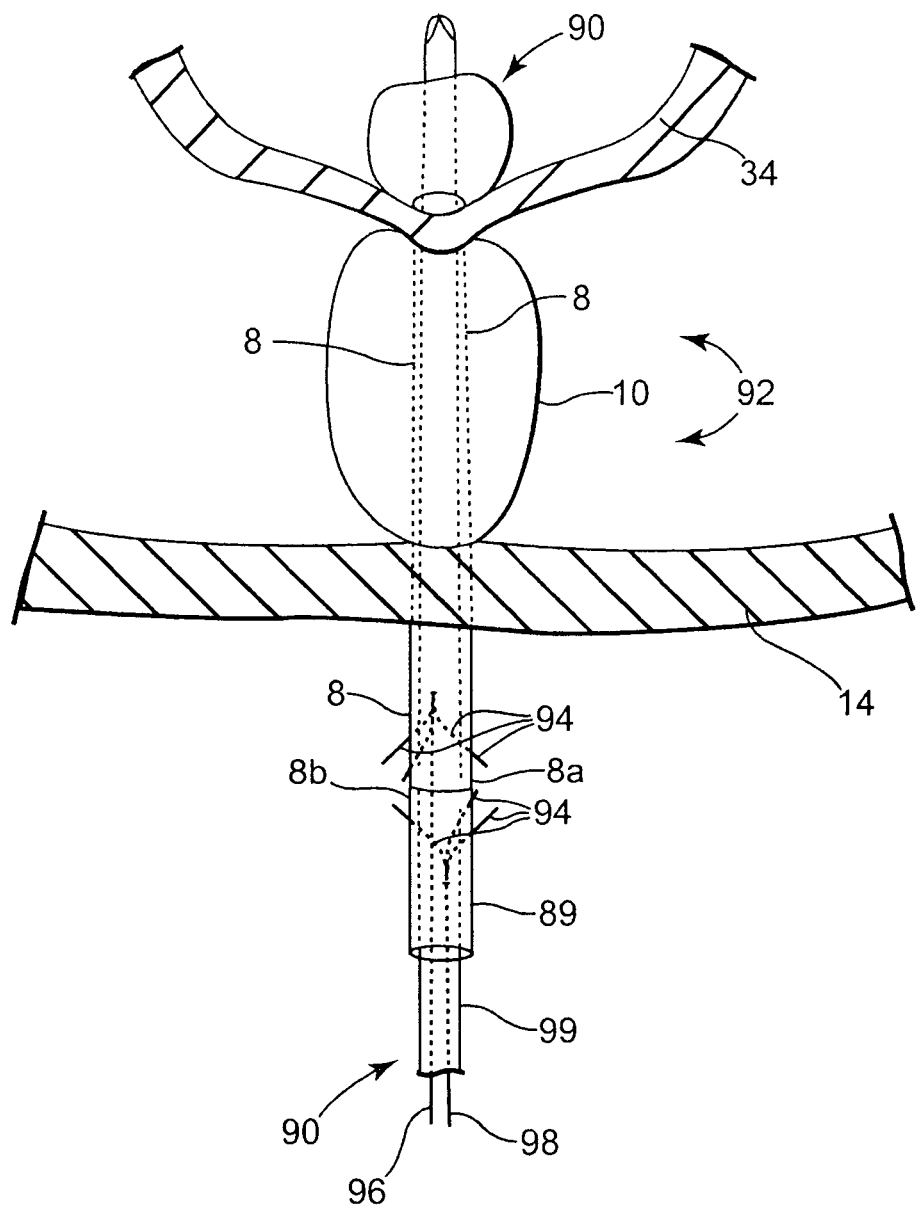

FIG. 9a illustrates the extended distal and proximal sets of tines 94 extending into opposing portions of severed urethra 8 and holding the severed tissue portions 8a and 8b in contact for healing. The tines contact and move the portions together for healing. The installed device also includes a balloon in bladder 34 and drainage means that function together to cause urine to pool in the bladder and drain from the bladder. Thus, the illustrated device may be left installed, including the tissue approximating structure, during the healing period. As will be appreciated, other embodiments of the device may also be used in an end-to-end anastomosis procedure, such as other embodiments illustrated herein, including devices that include a single set of tines similar to the tines of FIGS. 5 and 6.

Figure 9B:
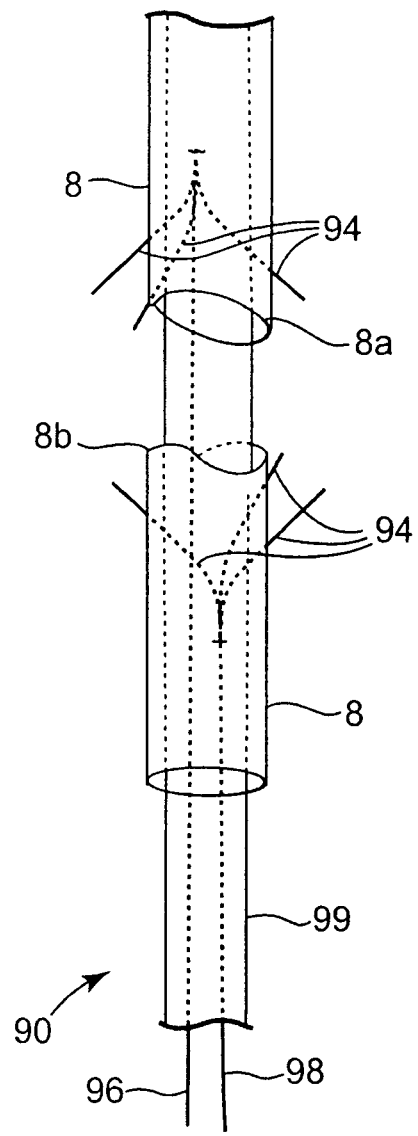
Figure 9C:
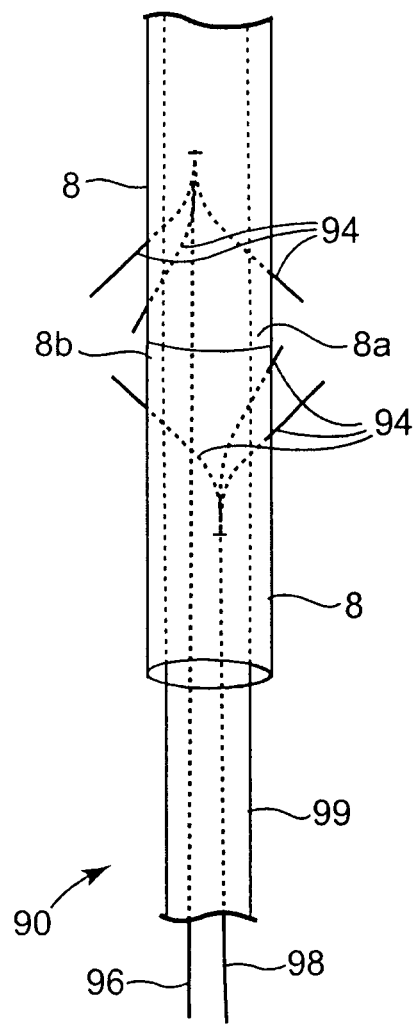

FIGS. 9b and 9c are close-up illustrations of the tissue approximating structures of FIGS. 9 and 9a, respectively, for clarity. As is illustrated in close-up FIGS. 9b and 9c, tines 94 can be extended from catheter body 90 to penetrate into and optionally (although perhaps not preferably) through urethral tissue 8. The opposing severed urethral tissues are brought together (optionally with the assistance of the opposing tines) and are held together as shown in FIG. 9c preferably for a time sufficient to cause healing together of the severed tissues while the anastomosis device is installed and functions to drain urine from the bladder.

An anastomosis device as described herein can remain installed in the patient during the time required for healing of the two tissue surfaces together, during which time the balloon remains inflated to prevent urine from passing through the bladder neck. The healing period can be considered the time period taken for severed tissue to achieve a water tight anastomosis. The healing period can depend on many factors such as the type of operation and the patient, and can take, e.g., from possibly as little as one or two days, up to possibly two months, with periods of from two to four weeks being sometimes typical.

While the device is installed, urine accumulates and pools inside of the bladder and can be drained from the bladder, preferably through drainage apertures and a drainage lumen within the anastomosis device, flowing to the proximal end of the device for collection. Such preferred embodiments of the inventive devices and methods offers the advantage of providing a single anastomosis device that functions to allow the severed tissue surfaces to heal together by use of the tissue approximating structure, without sutures, while at the same time providing a draining mechanism. The advantage of not requiring sutures for holding the severed tissues together or for healing can offer cost savings and eliminate complications by significantly reducing procedure time, thus reducing costs, and also reducing the length of time a patient is anesthetized. Sutures do not have to be removed, but instead, the tissue approximating structures of the anastomosis device can be retracted or deflated, and the device can be removed after healing.

Following is one series of more detailed exemplary steps useful according to the methods of the invention, for using the inventive anastomosis device to perform a prostatectomy.

1. Perform a radical prostatectomy by any method such as retropubic, laparoscopic, or transperineal, until prior to the vesico-urethral anastomosis. The following description is in the context of a retropubic radical prostatectomy, and with reference to an embodiment of the inventive device as illustrated at FIGS. 4 and 4a.
2. Close the bladder neck to the desired size via a purse-string suture.
3. The AD can be inserted into the bladder prior to the suturing to help determine the desired size or the bladder can be sutured independently.
4. Insert the AD through the meatus until it exits the urethral stump in the open abdomen.
5. Pull the AD until enough length has been exposed to reach the bladder.
6. Insert the AD into the bladder and inflate the balloon.
7. Extend the top (distal) tines of the AD and visually ensure that the tines do not penetrate the ureters of the bladder. This can be facilitated by extending and retracting the tines and seeing the "bump" form on the exterior wall of the bladder. The AD may also have visual markers on the external wall of the AD proximal to the top tines to mark the location of the tines.
8. The bladder can then be lowered to the perineal floor by releasing the traction on the bladder and physically moving it down by hand while lightly maintaining tension on the AD.
9. Once the bladder has been drawn to contact the urethral stump, a light tension can be placed on the AD while the proximal tines are extended into the perineal floor.
10. The bladder can then be filled using the drainage port on the AD and the anastomosis site can be checked for leaks.
11. If a leak is experienced the AD can be repositioned until the desired performance is reached.
12. The AD can remain in place for a time depending on the healing needs of the individual patient.

The invention claimed is:

1. A method of performing urethral anastomosis, the method comprising
   inserting a portion of an anastomosis device into a urethra through a meatus, the anastomosis device comprising a distal end comprising a balloon and elongate tissue approximating structure located on a proximal side of the balloon,
   inflating the balloon in the bladder, and
   using the tissue approximating structure to hold severed tissue together during healing,
wherein the tissue approximating structure comprises multiple tines.

2. The method of claim 1 comprising vesico-urethral anastomosis, the method comprising
   removing a prostate to leave a urethral stump and a bladder neck on a bladder,
   inserting a portion of the anastomosis device through the urethral stump and through the bladder neck into the bladder,
   moving the bladder neck to contact the urethral stump, and
   using the tissue approximating structure to hold the urethral stump against the bladder neck to allow healing of the urethral stump to the bladder neck.

3. The method of claim 2 comprising using the tissue approximating structure to hold the urethral stump in contact with the bladder neck for a time sufficient to allow the urethral stump and the bladder neck to heal together.

4. The method of claim 1 comprising end-to-end urethral anastomosis, the method comprising
   severing a urethra to produce two opposing severed urethral portions,
   moving the two opposing severed urethral portions into contact, and
   using the tissue approximating structure to hold the two opposing severed urethral portions in contact to allow the tissue portions to heal together.

5. The method of claim 4 comprising using the tissue approximating structure to hold the opposing severed urethral portions together for a time sufficient to allow the severed urethral portions to heal together.

6. The method of claim 1, comprising
   severing a urethra to leave opposing severed urethral tissues,
   inserting a distal end of the anastomosis device through the urethra and into the bladder,
   holding the opposing severed urethral tissues together in healing contact using the tissue approximating structure.

7. The method of claim 6 comprising performing a radical prostatectomy, the method comprising
   removing a prostate to leave a urethral stump and a bladder neck,
   inserting the anastomosis device through the urethral stump and through the bladder neck,
   holding the urethral stump and the bladder neck together in healing contact using the tissue approximating structure.

8. The method of claim 7 wherein the anastomosis device remains in place for a time to effect healing of the urethra stump to the bladder neck.

9. The method of claim 7 wherein the urethral anastomosis is an end-to-end urethral anastomosis comprising severing the urethra below a perineal wall and re-connecting the severed tissue.

10. The method of claim 6 comprising filling the bladder using a drainage port on the distal end and checking for leaks at the anastomosis site.

11. The method of claim 6 wherein the anastomosis device comprises
    an elongate flexible catheter body from which extend the tissue approximating structure and the balloon,
    the anastomosis device further comprising a drainage aperture at a distal end of the flexible catheter body, the drainage aperture connected to the proximal end through a drainage lumen, wherein the tissue approximating structure is located on the flexible catheter body on a proximal side of the balloon and on a proximal side of the drainage aperture.

12. The method of claim 1 wherein the anastomosis device comprises
    an elongate flexible catheter body comprising a distal end from which extend the tissue approximating structure and the balloon,
    the anastomosis device further comprising a drainage aperture at the distal end of the flexible catheter body connected to a proximal end through a drainage lumen, wherein the elongate tissue approximating structure is located on the flexible catheter body on a proximal side of the balloon and on a proximal side of the drainage aperture.

13. The method of claim 1 wherein the distal end of the anastomosis device comprises a drainage aperture connected to a proximal end of the device by a drainage lumen, and the method comprises draining the bladder through the drainage lumen.

14. The method of claim 1 comprising extending the tissue approximating structure from a fixed location, the fixed location being fixed relative to the distal end of the device and relative to a proximal end of the device.

15. A method of performing urethral anastomosis, the method comprising
    inserting a portion of an anastomosis device into a urethra through a meatus, the anastomosis device comprising a distal end comprising a balloon and elongate tissue approximating structure located on a proximal side of the balloon,
    inflating the balloon in the bladder,
    using the tissue approximating structure to hold severed tissue together during healing,
    using the tissue approximating structure to hold severed tissue together during healing, and
    after healing, retracting the tissue approximating structure into the anastomosis device and removing the anastomosis device from the urethra.

16. A method of performing urethral anastomosis, the method comprising
    inserting a portion of an anastomosis device into a urethra through a meatus, the anastomosis device comprising a distal end comprising a balloon and elongate tissue approximating structure located on a proximal side of the balloon,
    inflating the balloon in the bladder, and
    using the tissue approximating structure to hold severed tissue together during healing,
    using the tissue approximating structure to hold severed tissue together during healing for a period of time of about two to eight weeks, and
    after healing, retracting the tissue approximating structure into the anastomosis device and removing the anastomosis device from the urethra.

17. A method of performing urethral anastomosis, the method comprising
    inserting a portion of an anastomosis device into a urethra through a meatus, the anastomosis device comprising a distal end comprising a balloon and elongate tissue approximating structure located on a proximal side of the balloon,
    inflating the balloon in the bladder, and
    using the tissue approximating structure to hold severed tissue together during healing
    wherein the elongate tissue approximating structure located on a proximal side of the balloon comprises distal tissue approximating structure and proximal tissue approximating structure at fixed locations, the fixed locations being fixed relative to the distal end of the device and relative to a proximal end of the device.

18. The method of claim 17 wherein the distal tissue approximating structure and a the proximal tissue approximating structure comprise opposing sets of tines.

19. A method of performing urethral anastomosis, the method comprising
   inserting a portion of an anastomosis device into a urethra through a meatus, the anastomosis device comprising a distal end comprising
      a drainage aperture, the drainage aperture connected to a proximal end of the device by a drainage lumen, and
      elongate tissue approximating structure on a proximal side of the drainage aperture,
   inserting the drainage aperture in the bladder,
   using the tissue approximating structure to hold severed tissue together during healing, and
   draining the bladder through the drainage lumen,
wherein the elongate tissue approximating structure on a proximal side of the drainage aperture comprises distal tissue approximating structure and proximal tissue approximating structure at fixed locations, the fixed locations being fixed relative to the distal end of the device and relative to a proximal end of the device.

20. The method of claim 19 wherein the anastomosis device further comprises an expandable bladder sealer capable of expanding within the bladder to prevent urine from passing through the bladder neck and urethra to an anastomosis site, and the method comprises sealing the bladder by expanding the bladder sealer within the bladder.

21. The method of claim 20 wherein the bladder sealer comprises an inflatable balloon.

22. The method of claim 19 comprising using the tissue approximating structure to hold severed tissue together during healing, and after healing, retracting the tissue approximating structure into the anastomosis device and removing the anastomosis device from the urethra.

23. The method of claim 19 comprising using the tissue approximating structure to hold severed tissue together during healing for a period of time of about two to eight weeks, and after healing, retracting the tissue approximating structure into the anastomosis device and removing the anastomosis device from the urethra.

24. The method of claim 19 comprising extending the tissue approximating structure from a fixed location, the fixed location being fixed relative to the distal end of the device and relative to a proximal end of the device.

25. The method of claim 19 wherein the distal tissue approximating structure and a the proximal tissue approximating structure comprise opposing sets of tines.

26. A method of performing urethral anastomosis, the method comprising
   inserting a portion of an anastomosis device into a urethra through a meatus, the anastomosis device comprising
      a distal end comprising first tissue approximating structure and elongate second tissue approximating structure, and
   extending the first tissue approximating structure within the bladder, and
   using the elongate second tissue approximating structure to hold severed tissue together during healing
wherein
   the first tissue approximating structure is selected from the group consisting of a balloon and a balloon-like structure,
   the elongate second tissue approximating structure comprises a distal tissue approximating structure and a proximal tissue approximating structure, and
   the first tissue approximating structure and the second tissue approximating structure are at fixed locations, the fixed locations being fixed relative to the distal end of the device and relative to a proximal end of the device.

27. The method of claim 26 wherein the elongate second tissue approximating structure comprises movable elongate structure selected from a tine, a probe, a prod, and a needle.

28. The method of claim 26 comprising extending the first tissue approximating structure to contact bladder tissue and prevent urine from contacting an anastomosis site.

29. The method of claim 26 comprising using the elongate second tissue approximating structure to hold severed tissue together during healing, and after healing, retracting the elongate second tissue approximating structure into the anastomosis device and removing the anastomosis device from the urethra.

30. The method of claim 26 comprising using the elongate second tissue approximating structure to hold severed tissue together during healing for a period of time of about two to eight weeks, and after healing, retracting the elongate second tissue approximating structure into the anastomosis device and removing the anastomosis device from the urethra.

31. The method of claim 26 wherein the distal end of the anastomosis device comprises a drainage aperture connected to a proximal end of the device by a drainage lumen, and the method comprises draining the bladder through the drainage lumen.

32. The method of claim 26 comprising extending the tissue approximating structure from a fixed location, the fixed location being fixed relative to the distal end of the device and relative to a proximal end of the device.

33. The method of claim 26 wherein the distal tissue approximating structure and a the proximal tissue approximating structure comprise opposing sets of tines.

* * * * *